United States Patent [19]

Garcia et al.

[11] Patent Number: 5,624,933

[45] Date of Patent: Apr. 29, 1997

[54] PROCESS FOR THE PREPARATION OF A 6-FLUORO-2-HALO-QUINOLINE

[75] Inventors: Herve Garcia, Communay; Roland Jacquot, Sainte Foy les Lyon; Patrick Leon, Tassin la Demi Lune, all of France

[73] Assignee: Rhone-Poulenc Rorer S.A., Antony, France

[21] Appl. No.: 448,404

[22] PCT Filed: Oct. 20, 1994

[86] PCT No.: PCT/US94/11832

§ 371 Date: Jun. 7, 1995

§ 102(e) Date: Jun. 7, 1995

[87] PCT Pub. No.: WO94/24113

PCT Pub. Date: Oct. 27, 1994

[30] Foreign Application Priority Data

Apr. 8, 1993 [FR] France .................... 93 04163

[51] Int. Cl.$^6$ .................... H01N 43/42; C07D 215/20; C07D 413/00
[52] U.S. Cl. .................... 514/292; 514/312; 544/36; 544/60; 544/96; 544/126; 544/238; 544/361; 546/81; 546/101; 546/110; 546/156; 546/157; 546/170; 546/249; 546/258
[58] Field of Search .................... 546/81, 101, 110, 546/156, 157, 170, 249, 258; 544/36, 60, 96, 126, 238, 361; 514/292, 312

[56] References Cited

U.S. PATENT DOCUMENTS

| | | | |
|---|---|---|---|
| 4,190,659 | 2/1980 | Hardtmann | 424/258 |
| 4,710,507 | 12/1987 | Campbell et al. | 546/157 |
| 4,948,894 | 8/1990 | Moran et al. | 546/95 |
| 4,970,213 | 11/1990 | Antoine et al. | 546/81 |
| 4,973,590 | 11/1990 | Preiss et al. | 546/156 |
| 4,990,515 | 2/1991 | Antoine et al. | 546/81 |
| 5,004,745 | 4/1991 | Antoine et al. | 544/361 |
| 5,053,509 | 10/1991 | Antoine et al. | 544/361 |
| 5,442,070 | 8/1995 | Daubie et al. | 546/156 |
| 5,484,921 | 1/1996 | Daubie et al. | 546/81 |

FOREIGN PATENT DOCUMENTS

| | | |
|---|---|---|
| 0148623 | 7/1985 | European Pat. Off. . |
| 0236140 | 9/1987 | European Pat. Off. . |
| 0379412 | 7/1990 | European Pat. Off. . |
| 2225166 | 11/1974 | France . |
| WO93/07127 | 4/1993 | WIPO . |

*Primary Examiner*—John C. Bleutoe
*Assistant Examiner*—Randy Gulakowski
*Attorney, Agent, or Firm*—Finnegan, Henderson, Farabow, Garrett & Dunner, L.L.P.

[57] ABSTRACT

Method of preparation of 6-fluoro-2-halogen quinoline of general formula (I) wherein R is a hydrogen atom or an alkyl radical and Hal and Hal' are identical or different halogen atoms. The invention is characterized in that a halogenating agent is made to act on hydroxy-1 quinoline of general formula (II) wherein Hal is defined as above and $R_1$ is defined as R excepting a hydrogen atom, the acid function being optionally released if a 6-fluoro-2-halogen quinoline is to be obtained for which R is a hydrogen atom.

8 Claims, No Drawings

PROCESS FOR THE PREPARATION OF A 6-FLUORO-2-HALO-QUINOLINE

The present invention relates to the preparation of a 6-fluoro-2-haloquinoline of general formula:

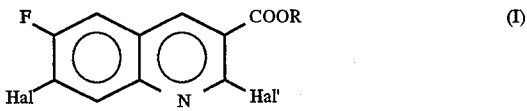

in which R is a hydrogen atom or an alkyl radical, and Hal and Hal' are identical or different halogen atoms.

U.S. Pat. No. 4,970,213 has described 6-fluoro-2-chloroquinolinecarboxylic acids of structure:

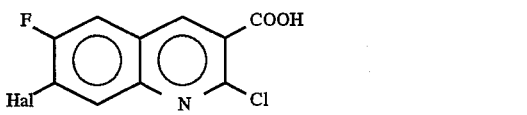

in which Hal is a fluorine or chlorine atom, which are useful as intermediates for the preparation of 1,8-benzonaphthyridines having an antimicrobial activity.

The process according to the present invention is also useful for the preparation of antimicrobial 1,8-benzonaphthyridine derivatives, and it furthermore makes it possible to work under mild conditions and to obtain improved yields and avoids proceeding via unstable intermediate products.

In the general formula (I) when R represents an alkyl radical, the latter is straight or branched and contains 1 to 4 carbon atoms; the symbol Hal is advantageously chosen from chlorine or fluorine and the symbol Hal' is chosen from chlorine or bromine.

According to the present invention, the quinoline derivative of general formula (I) may be prepared by the action of a halogenating agent on the 1-hydroxyquinolone of general formula:

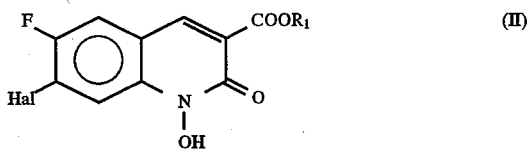

in which Hal is defined as above and $R_1$ is defined as R with the exception of representing a hydrogen atom, optionally followed by freeing the acidic function if it is desired to obtain a quinoline derivative of general formula (I) for which R is a hydrogen atom.

The reaction is carried out in an organic solvent such as, for example, a halogenated solvent (particularly a chlorinated solvent such as dichloromethane, 1,2-dichloroethane, 1,1,1-trichloroethane, chlorobenzene or dichlorobenzene especially) or in an aromatic solvent (for example toluene, nitrobenzene, diphenyl ether, etc.) at a temperature between 20° C. and the reflux temperature of the reaction mixture.

When it is desired to obtain 2-chloroquinoline, the halogenating agent may be chosen from phosphorus trichloride, phosphorus pentachloride, thionyl chloride, sulphuryl chloride, sulphur dichloride, stannous chloride, cuprous chloride, titanium trichloride, ferrous chloride, chromium (II) chloride, triphenylphosphine hydrochloride, dichlorotriphenylphosphorane or chlorine. When it is desired to obtain 2-bromoquinoline, the halogenating agent may be chosen from phosphorus tribromide, triphenylphosphine hydrobromide or dibromotriphenylphosphorane.

In the cases where the ester has been obtained and where it is desired to obtain the acid of general formula (I) for which R is a hydrogen atom, hydrolysis of the ester may be carried out by any known method for obtaining an acid from an ester without affecting the remainder of the molecule. The hydrolysis is in particular carried out in acidic medium, for example in the presence of hydrochloric acid, sulphuric acid or methanesulphonic acid. It may also be carried out in basic aqueous-alcoholic medium (for example sodium hydroxide or potassium hydroxide).

The 1-hydroxyquinolone of general formula (II) may be obtained by cyclization of a nitro derivative of general formula:

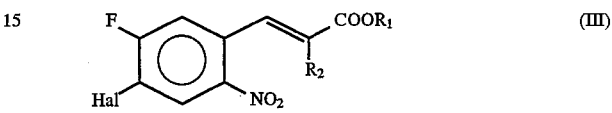

in which Hal and $R_1$ are defined as above, and $R_2$ is defined as $R_1$ or represents a carbamoyl or cyano radical, by catalytic hydrogenation in acidic medium.

The catalytic hydrogenation is carried out in the presence of palladium on charcoal or platinum, at a temperature between 0° and 130° C., in the presence of an organic or inorganic acid which does not alter the remainder of the molecule. By way of example, the process is performed in acetic acid or in formic acid, and it is also possible to perform the process using dilute hydrochloric acid or dilute sulphuric acid in an aqueous-alcoholic medium. The reaction is carried out until the hydrogen consumption decreases sharply. The process is preferably carried out at atmospheric pressure.

The nitro derivative of general formula (III) may be prepared by the action of a malonic acid derivative of general formula:

$$R_1OCO—CH_2—R_2 \quad\quad (IV)$$

in which $R_1$ and $R_2$ are defined as above, on a nitrobenzaldehyde derivative of general formula:

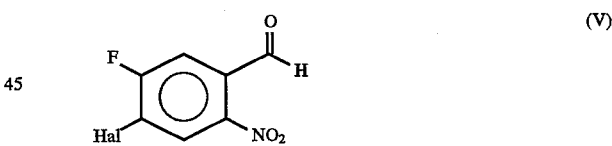

in which Hal is defined as above.

The reaction is generally carried out in basic medium [for example in the presence of an alkali metal bicarbonate (sodium bicarbonate), a hydride (sodium hydride) or an alkoxide at a temperature between 0° and 150° C., in an organic solvent such as an anhydride (acetic anhydride for example) or such as an amide (dimethylformamide or N-methylpyrrolidone for example) by performing the process in the presence of molecular sieves or any other drying agent] or alternatively in a mixture of solvents such as a polar aprotic solvent/acetic anhydride mixture (dimethylformamide/acetic anhydride or N-methylpyrrolidone/acetic anhydride for example). It is also possible to perform the process in a two-phase medium. It is not essential to isolate the product of general formula (III) in order to use it in the following reaction.

The fluoronitrobenzaldehyde of general formula (V) is obtained by nitration of the fluorobenzaldehyde of general formula:

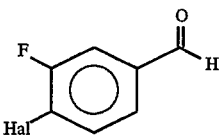

in which Hal is defined as above.

The reaction is advantageously carried out using concentrated nitric acid in the form of a sulphonitric mixture, or in the form of a nitric acid/acetic acid mixture, at a temperature between 0° and 90° C.

4-Chloro-3-fluorobenzaldehyde may be prepared according to the method described in European Application EP 289,942.

According to the invention, the preparation of the 6-fluoro-2-haloquinoline of general formula (I) is useful for the synthesis of derivatives of 1,8-benzo[b]naphthyridine of general formula:

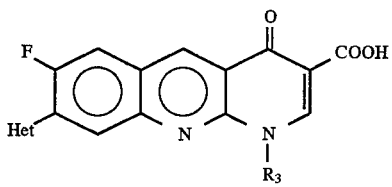

in which either $R_3$ (which represents an alkyl, fluoroalkyl, cycloalkyl containing 3 to 6 carbon atoms, alkyloxy or alkylamino radical) and Het (which is a nitrogen-containing heterocyclic radical) are as defined for the substituents in the 1- and 8-positions, in the European Application EP 431,991 and the U.S. Pat. No. 5,004,745, or $R_3$ is a hydrogen atom or an alkyl, fluoroalkyl, carboxyalkyl, cycloalkyl containing 3 to 6 carbon atoms, fluorophenyl, difluorophenyl, alkyloxy or alkylamino radical, and Het is a 1-azetidinyl radical which is substituted [in the 3-position with a radical $R_4$ which may be a hydrogen atom or a hydroxyl, amino or alkylamino radical in which the alkyl part is optionally substituted with an amino or hydroxyl radical or may represent a dialkylamino radical for which the alkyl parts may optionally form, with the nitrogen atom to which they are attached, a 5- or 6-membered heterocycle optionally containing another hetero atom chosen from nitrogen, oxygen or sulphur, or may represent a cycloalkylamino radical containing 3 to 6 members, or an alkanoylamino, N-alkyl-N-alkanoylamino or aminoalkylphenylamino radical, and substituted in the 2- and 3-positions with radicals $R_5$ and $R_6$, which may be identical or different and which represent hydrogen atoms, alkyl radicals, alkenyl radicals containing 2 to 4 carbon atoms, phenyl radicals or phenyl radicals substituted with a halogen atom, or with an alkyl, alkyloxy, hydroxyl, nitro, amino, alkylamino, dialkylamino or haloalkyl radical, or alternatively disubstituted in the 2-position with radicals $R_5$ and $R_6$ which represent alkyl radicals], it being understood that the alkyl and alkanoyl radicals mentioned above are straight or branched and contain 1 to 4 carbon atoms.

These benzonaphthyridine derivatives are particularly advantageous antimicrobial agents.

The 1,8-benzo[b]naphthyridines of general formula (VII) may be obtained by the process according to the invention, by working in the following way:

The benzonaphthyridine derivative of general formula (VII) may be obtained from 2-chloro- (or 2-bromo-) 6-fluoroquinolinecarboxylic acid of general formula (I) in which R is a hydrogen atom, according to or by analogy with the method described in the Application EP 431,991 or WO 93/07144, or in the U.S. Pat. No. 5,004,745 or U.S. Pat. No. 4,970,213.

The benzonaphthyridine derivative of general formula (VII) may also be obtained from the ester of general formula (I) for which R is an alkyl radical, by working as follows:

An amine of general formula:

$$R_3\text{—NH—CH}_2\text{—CH}_2\text{—R}_7 \qquad \text{(VIII)}$$

in which $R_3$ is defined as above and $R_7$ is an alkyloxycarbonyl, cyano, carbamoyl, alkylcarbamoyl, benzylcarbamoyl, hydroxyethylcarbamoyl, dialkylaminoethylcarbamoyl or dialkylcarbamoyl radical in which the alkyl parts may optionally form, with the nitrogen atom to which they are attached, a 5- or 6-membered heterocycle optionally containing another hetero atom chosen from oxygen, sulphur or nitrogen and optionally substituted on the nitrogen with an alkyl radical (the alkyl radicals being straight or branched and containing 1 to 4 carbon atoms), is condensed with the halofluoroquinoline of general formula (I) in which R is an alkyl radical, so as to obtain a fluoro ester of general formula:

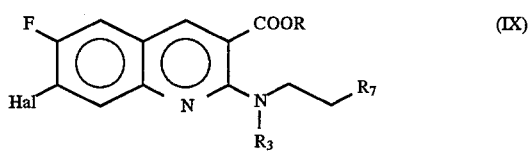

in which Hal, $R_3$ and $R_7$ are defined as above and R represents an alkyl radical.

The condensation is carried out in basic medium in an organic solvent such as an aromatic hydrocarbon (toluene for example), an amide (dimethylformamide or N-methylpyrrolidone for example), an ether (tetrahydrofuran for example), a sulphoxide (dimethyl sulphoxide for example), a chlorinated solvent (dichloromethane, dichloroethane or chlorobenzene for example) or an alcohol at a temperature between –10° and 120° C.

By way of example, the bases used may be chosen from alkali metal carbonates (sodium or potassium carbonate), alkoxides or an alkali metal hydride (sodium hydride).

It is understood that, in the variant where the symbol $R_3$ represents a carboxyalkyl radical, the latter is protected prior to the reaction. Removal of the protecting radical is preferably carried out after the oxidation reaction, on the benzonaphthyridine derivative of general formula (XI) described below. The protection and the freeing of the acid function are carried out according to the usual methods which do not alter the remainder of the molecule. In particular according to the methods which have been mentioned above.

The fluoroquinoline of general formula (IX) is cyclized in basic medium in order to prepare the 1,2,3,4-tetrahydro-1,8-benzo[b]naphthyridine of general formula:

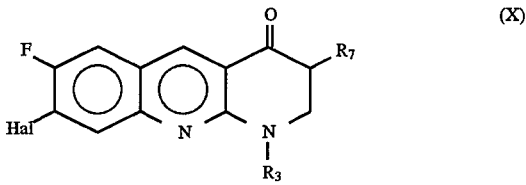

in which Hal, $R_3$ and $R_7$ are defined as above.

The reaction is carried out at a temperature between –70° and 120° C. in the presence of a base such as an alkoxide (sodium ethoxide, sodium methoxide or potassium t-butoxide for example), an alkali metal hydride (sodium hydride for example), or alternatively an alkali metal hydroxide by performing the process by phase transfer. The process is advantageously carried out in a polar aprotic solvent (for example dimethylformamide or tetrahydrofuran) or in an alcohol (ethanol or methanol for example), in a glyme or in a glycol (ethylene glycol for example). When the reaction is carried out by phase transfer, the process is advantageously performed in a chlorinated solvent such as methylene chloride, the base being in solution in the aqueous phase.

The 1,2,3,4-tetrahydro-1,8-benzo[b]naphthyridine of general formula (X) is oxidized in order to prepare the 1,8-benzo[b]naphthyridine of general formula:

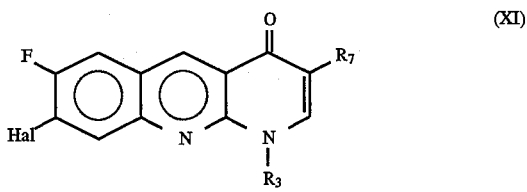

in which

Hal, $R_3$ and $R_7$ are defined as above.

The oxidation is carried out using hydrogen peroxide, optionally in the presence of potassium iodide, in an organic solvent such as an alcohol (ethanol for example), at a temperature between 0° and 120° C. It is also possible to perform the process in a two-phase medium in a water/chlorinated solvent (dichloromethane, dichloroethane, etc.) mixture.

The heterocycle Het is condensed with the 1,8-benzo[b] naphthyridine of general formula (XI) or the corresponding acid in order to prepare a benzonaphthyridine derivative of general formula (VII), by performing the process according to or by analogy with the methods described in European Application EP 431,991 and the U.S. Pat. No. 5,004,745 followed, where appropriate, by conversion of the ester, the amide or the nitrile obtained to an acid of general formula (VII). The benzonaphthyridine derivatives of general formula (VII) are antimicrobial agents whose activities have been described in the European Application and the American Patent mentioned above. The benzonaphthyridine derivatives of general formula (VII) for which Het is an azetidinyl radical, which are defined in greater detail in the International Application WO 93/07144, also display antibacterial properties. They show a remarkable in vitro and in vivo activity on Gram-positive germs and also on Gram-negative germs. In vitro, they are active at a concentration between 0.06 and 4 µg/cm³ on *Staphylococcus aureus* IP 8203 and at a concentration between 0.25 and 20 µg/cm³ on *Escherichia coli* strain NIHJ JC2. In vivo, they are active on mice experimentally infected with *Staphylococcus aureus* IP 8203 at doses of between 10 and 200 mg/kg via the oral route.

The products arising from the process according to the present invention, as well as the products to which they lead, may optionally be purified by physical methods such as crystallization or chromatography.

The examples which follow, given without any limitation being implied, illustrate the present invention.

EXAMPLE 1

15.0 g of 3-ethoxycarbonyl-6,7-difluoro-1-hydroxy-2-oxoquinoline (assay 90% - 50.1 mmol) [containing 10 mol % of 3-ethoxycarbonyl-6,7-difluoro-2-oxoquinoline] and 100 cm³ of 1,2-dichloroethane are placed under an argon atmosphere, followed by addition thereto of 22 cm³ of phosphorus trichloride (251 mmol), and brought to reflux. After stirring the reaction mixture for 3 hours 30 minutes, 5.5 cm³ of phosphoryl chloride (59 mmol) are added and heating at reflux is again carried for 3 hours 30 minutes. The reaction mixture is poured onto 300 g of ice and stirred for 15 minutes. After separation of the phases after settling, the aqueous phase is extracted with twice 50 cm³ of 1,2-dichloroethane, and the organic phases are combined and washed with 200 cm³ of saturated sodium bicarbonate solution, followed by 150 cm³ of water and finally with 150 cm³ of saturated sodium chloride solution. After drying and concentration to dryness, 13.4 g of 2-chloro-3-ethoxycarbonyl-6,7-difluoroquinoline are obtained, in the form of a cream-coloured solid. (HPLC assay: >99%; Y %=88%).

The product obtained may be purified by recrystallization: a portion of the solid obtained: 7.0 g, is dissolved at 90° C. in 157 cm³ of a mixture of 95% ethanol and water (60/40 by volume). The mixture is left to cool at room temperature, with stirring. The precipitate is washed with 10 cm³ of ice water, with 10 cm³ of a water/ethanol mixture (4/1 by volume), and then with 3 times 25 cm³ of ice water and dried under reduced pressure over $P_2O_5$. 6.58 g of 2-chloro-3-ethoxycarbonyl-6,7-difluoroquinoline are thus obtained, in the form of a white solid melting at 111°–112° C. (capillary). (HPLC assay: 100%; Y %=94%).

3-Ethoxycarbonyl-6,7-difluoro-1-hydroxy-2-oxoquinoline may be prepared in the following way:

130 g of acetic acid and 1 g of palladium on charcoal at a palladium content of 5% are introduced into a 40 cm³ reactor. The reactor is purged with a stream of nitrogen and then, with stirring and at atmospheric pressure, a stream of hydrogen (3 liters/hour) is passed in while heating to 55° C. When the temperature of 55° C. is reached, 128.5 g of the 21.5% solution of ethyl (3,4-difluoro-6-nitrobenzylidene) malonate are added over 35 minutes. The temperature is maintained at 55° C. throughout the injection. 5 minutes after the end of the addition, the hydrogen consumption decreases sharply. The apparatus is purged with a stream of nitrogen for 10 minutes. The catalyst is filtered off. 300 g of deionized water are added to the filtrate over 10 minutes. The suspension obtained is stirred for 1 hour at 20° C. and the solids are then filtered off and washed with 3 times 50 cm³ of deionized water. The filter cake is oven-dried at 40° C. under reduced pressure (13.3 kPa) for 4 hours. 17.7 g of 3-ethoxycarbonyl-6,7-difluoro-1-hydroxy-2-oxoquinoline are thus obtained in 90% purity (comprising 10% of 3-ethoxycarbonyl-6,7-difluoro-2-oxoquinoline), melting with decomposition at 215°–218° C.

Ethyl (3,4-difluoro-6-nitrobenzylidene)malonate may be prepared in the following way:

31.82 g of 3,4-difluoro-6-nitrobenzaldehyde (assay 90%; 153 mmol) are placed under argon at 20° C. with 32.80 g of ethyl malonate (204 mmol) and 60 cm³ of acetic anhydride. 28.56 g of sodium bicarbonate (340 mmol) are added with stirring. The suspension is maintained for 2 hours at approximately 20° C., and the orange-coloured heterogeneous mixture is then heated for 3 hours at a temperature of approximately 70° C. After cooling to 52° C., 60 cm³ of acetic acid are poured in, followed at room temperature (20° C.) by 30 cm³ of water. Stirring is continued overnight at this temperature. 234.4 g of a dark-orange solution of ethyl (3,4-difluoro-6-nitrobenzylidene)malonate at a concentration (by weight) of 21.5% are thus obtained, which solution is used as it is in the following step.

3,4-Difluoro-6-nitrobenzaldehyde is prepared in the following way:

To 520 cm³ of sulphuric acid, cooled to 0° C., are added, with stirring, 60 cm³ of fuming nitric acid, over 30 minutes. 100 g of 3,4-difluorobenzaldehyde are added over 30 minutes at approximately 0° C. to the solution obtained. The temperature is allowed to return to approximately 20° C. and stirring is continued for 3 hours at this temperature. After cooling to approximately 5° C., the reaction mixture is poured, over 30 minutes and with vigorous stirring, onto 1200 g of crushed ice. The temperature is allowed to return to approximately 20° C., followed by extraction with twice 600 cm³ of toluene. The combined organic extracts are washed with 3 times 1000 cm³ of water, and concentrated under reduced pressure (20 kPa) at 50° C. 113 g of 3,4-difluoro-6-nitrobenzaldehyde are obtained in the form of a brown oil, which is used as it is in the subsequent syntheses. A purified sample of 3,4-difluoro-6-nitrobenzaldehyde gives the following characteristics:

BP(6.66 Pa)=46° C.

NMR spectrum (400 MHz, DMSO, T=298° K.) 10.20 ppm (1H, 1s); 8.5 ppm (1H, 1 q); 8.05 ppm (1H, 1q).

EXAMPLE 2

A mixture of 3-ethoxycarbonyl-6,7-difluoro-1-hydroxy-2-oxoquinoline (25 g at a concentration of 75 mol %, equivalent to 69.65 mmol), 3-ethoxycarbonyl6,7-difluoro-2-oxoquinoline (25 g at a concentration of 5 mol %, equivalent to 4.9 mmol), phosphorus trichloride (59.6 g, equivalent to 433.5 mmol) and phosphoryl chloride (15.05 g, equivalent to 98.05 mmol) in 1,2-dichloroethane (170 cm³) is heated at reflux for 3 hours. After cooling to 0° C., the reaction mixture is poured onto slushed ice (250 g of ice +250 g of water at 0° C.) and left to separate overnight. The organic phase is washed with saturated NaHCO₃ solution (100 cm³), followed by water (100 cm³), and then concentrated to dryness in order to obtain 19.8 g of 3-ethoxycarbonyl-6,7-difluoro-2-chloroquinoline of 90% assay (HPLC), equivalent to a yield of 88%.

The crude 3-ethoxycarbonyl-6,7-difluoro-2-chloroquinoline [7.0 g at a purity of 90% (HPLC assay)] is recrystallized in 157 cm³ of ethanol/water mixture (60/40 by volume) to give 5.5 g of pure 3-ethoxycarbonyl-6,7-difluoro-2-chloroquinoline, equivalent to a recrystallization yield of 88%.

EXAMPLE 3

By performing the process as in Example 2, but in 170 cm³ of toluene and with heating at reflux for 4 hours 15 minutes, 21.8 g of crude 3-ethoxycarbonyl-6,7-difluoro-2-chloroquinoline assaying at 85% are obtained, equivalent to a yield of 92%.

The products obtained by the process according to the invention may be used in the following way:
Example of use 1

2-Chloro-3-ethoxycarbonyl-6,7-difluoroquinoline is converted to 2-chloro-6,7-difluoro-3-quinolinecarboxylic acid according to the usual methods and may thus lead to the 1,8-benzo[b]-naphthyridine derivatives described in the U.S. Pat. No. 4,970,213.
Example of use 2

Preparation of 3-ethoxycarbonyl-6,7-difluoro-2-(N-methyl-N-β-ethoxycarbonylethyl)aminoquinoline:

To a solution of 72 g of 2-chloro-3-ethoxycarbonyl-6,7-difluoroquinoline prepared as described in Example 1 and 45.1 g of N-methyl-N-β-ethoxycarbonylethylamine in 750 cm³ of toluene are added 56.2 g of sodium carbonate. The suspension obtained is heated at approximately 90° C., and then stirred for 4 hours at this temperature. The reaction mixture is subsequently cooled to approximately 20° C. and then washed with 3 times 400 cm³ of water. The organic phase is concentrated to dryness under reduced pressure (20 kPa) at approximately 50° C. 94 g of 3-ethoxycarbonyl-6,7-difluoro-2-(N-methyl-N-β-ethoxycarbonylethyl) aminoquinoline are obtained in the form of an oil, which is used without further purification for the subsequent steps.

Preparation of 3-ethoxycarbonyl-7,8-difluoro-1-methyl-4-oxo-1,2,3,4-tetrahydro-1,8-benzo[b]naphthyridine:

To a solution of 26.6 g of sodium ethoxide brought to reflux in 900 cm³ of absolute ethanol is added, over 80 minutes, a solution of 94 g of 3-ethoxycarbonyl-6,7-difluoro-2-(N-methyl-N-β-ethoxycarbonylethyl) aminoquinoline in 300 cm³ of absolute ethanol. The suspension obtained is stirred for a further 15 minutes, still at reflux. 38 cm³ of glacial acetic acid are subsequently poured in over 30 minutes. The reaction mixture is stirred for a further 15 minutes, and then 500 cm³ of water are poured in over 45 minutes, still at reflux. The suspension obtained is cooled to approximately 20° C. The precipitate is filtered off at approximately 20° C. and washed with twice 300 cm³ of water. The moist product is dried under reduced pressure (20 kPa) at approximately 60° C. 71.5 g of 3-ethoxycarbonyl-7,8-difluoro-1-methyl-4-oxo-1,2,3,4-tetrahydro-1,8-benzo[b]naphthyridine are obtained, in the form of a yellow solid melting at 188° C.

Preparation of 3-ethoxycarbonyl-7,8-difluoro-1-methyl-4-oxo-1,4-dihydro-1,8-benzo[b]naphthyridine:

To a suspension of 71 g of 3-ethoxycarbonyl-7,8-difluoro-1-methyl-4-oxo-1,2,3,4-tetrahydro-1,8benzo[b] naphthyridine in 1000 cm³ of ethanol is added, with stirring at approximately 20° C., a solution of 3.78 g of potassium iodide in 20 cm³ of water. The suspension is heated at 77° C. and 30 cm³ of hydrogen peroxide at a concentration by weight of 33% are added over 60 minutes at this temperature. The reaction mixture is maintained at reflux for a further 30 minutes, followed by cooling to approximately 20° C. A solution of 11.4 g of sodium thiosulphate in 50 cm³ of water are poured in over 5 minutes at this temperature. The precipitate obtained is filtered off at approximately 20° C. and washed with twice 300 cm³ of water. The moist product obtained is dried under reduced pressure (20 kPa) at approximately 60° C. 73 g of 3-ethoxycarbonyl-7,8-difluoro-1-methyl-4-oxo-1,4-dihydro-1,8-benzo[b] naphthyridine are isolated, in the form of a white solid melting at a temperature greater than 270° C.
Example of use 3

Preparation of 3-ethoxycarbonyl-6,7-difluoro-2-(N-ethyl-N-β-ethoxycarbonylethyl)aminoquinoline:

To a solution of 10 g of 2-chloro-3-ethoxycarbonyl-6,7-difluoroquinoline prepared as described in Example 1 and 9.7 g of N-ethyl-N-β-ethoxycarbonylethylamine in 120 cm³ of toluene are added 7.8 g of sodium carbonate. The suspension obtained is heated at approximately 90° C. and then stirred for 4 hours at this temperature. The reaction mixture is subsequently cooled to approximately 20° C., followed by washing with 3 times 100 cm³ of water. The organic phase is concentrated to dryness under reduced pressure (20 kPa) at approximately 50° C. 13 g of 3-ethoxycarbonyl-6,7-difluoro-2-(N-ethyl-N-β-ethoxycarbonylethyl) aminoquinoline are obtained in the form of an oil, which is used without further purification for the subsequent steps.

Preparation of 3-ethoxycarbonyl-7,8-difluoro-1-ethyl-4-oxo-1,2,3,4-tetrahydro-1,8-benzo[b]naphthyridine:

To a solution of 16.1 g of sodium ethoxide brought to reflux in 600 cm³ of absolute ethanol is poured, over 60 minutes, a solution of 68 g of 3-ethoxycarbonyl-6,7-difluoro-2-(N-ethyl-N-β-ethoxycarbonylethyl) aminoquinoline in 200 cm³ of absolute ethanol. The suspension obtained is stirred for an additional 60 minutes, still at reflux. 20 cm³ of glacial acetic acid are subsequently poured in over 30 minutes. The reaction mixture is stirred for a further 15 minutes and then 400 cm³ of water are poured in over 45 minutes, still at reflux. The suspension obtained is cooled to approximately 20° C. The precipitate obtained is filtered off at approximately 20° C. and washed with twice 200 cm³ of water. The moist product is dried under reduced pressure (20 kPa) at approximately 50° C. 52.4 g of 3-ethoxycarbonyl-7,8-difluoro-1-ethyl-4-oxo-1,2,3,4-tetrahydro-1,8-benzo[b]naphthyridine are isolated, in the form of a golden-yellow solid melting at 152° C.

Preparation of 3-ethoxycarbonyl-7,8-difluoro-1-ethyl-4-oxo-1,4-dihydro-1,8-benzo[b]naphthyridine:

To a suspension of 33 g of 3-ethoxycarbonyl-7,8-difluoro-1-ethyl-4-oxo-1,2,3,4-tetrahydro-1,8-benzo[b]naphthyridine in 1000 cm³ of ethanol is added, with stirring at approximately 20° C., a solution of 1.7 g of potassium iodide in 10 cm³ of water. The suspension is heated at 77° C. and 12.7 cm³ of hydrogen peroxide at a concentration of 33% by weight is poured in at this temperature over 30 minutes. The reaction mixture is maintained at reflux for an additional 30 minutes, and then cooled to approximately 20° C. At this temperature, a solution of 6 g of sodium thiosulphate in 20 cm³ of water is poured in over 5 minutes. The precipitate obtained is filtered off at approximately 20° C. and is washed with twice 150 cm³ of water. The moist product obtained is dried under reduced pressure (20 kPa) at approximately 50° C. 28.7 g of 3-ethoxycarbonyl-7,8-difluoro-1-ethyl-4-oxo-1,4-dihydro-1,8-benzo[b]naphthyridine are isolated, in the form of a light yellow solid melting at 270° C.

Example of use 4

Preparation of 3-ethoxycarbonyl-6,7-difluoro-2-(N-cyclopropyl-N-β-ethoxycarbonylethyl)aminoquinoline:

To a solution of 3.48 g of 2-chloro-3-ethoxycarbonyl-6,7-difluoroquinoline prepared as described in Example 1 and 3 g of N-cyclopropyl-N-β-ethoxycarbonylethylamine in 10 cm³ of toluene are added 3 g of sodium carbonate. The suspension obtained is heated to reflux and then stirred for 15 hours at this temperature. The reaction mixture is subsequently cooled to approximately 20° C., followed by addition of 30 cm³ of water and 4.5 cm³ of acetic acid. After separation of the phases after settling, the reaction mixture is washed with twice 10 cm³ of water. The organic phase is concentrated to dryness under reduced pressure (20 kPa) at approximately 50° C. 3.3 g of crude 3-ethoxycarbonyl-6,7-difluoro-2-(N-cyclopropyl-N-β-ethoxycarbonylethyl) aminoquinoline are obtained in the form of an oil, which is used without further purification for the subsequent step.

Preparation of 3-ethoxycarbonyl-7,8-difluoro-1-cyclopropyl-4-oxo-1,2,3,4-tetrahydro-1,8-benzo[b]naphthyridine:

To a solution of 1.6 g of sodium ethoxide brought to reflux in 40 cm³ of absolute ethanol is added, over 60 minutes, a solution of 3-ethoxycarbonyl-6,7-difluoro-2-(N-cyclopropyl-N-β-ethoxycarbonylethyl)aminoquinoline in 20 cm³ of absolute ethanol. The solution obtained is stirred for an additional 60 minutes at reflux. 2.6 cm³ of glacial acetic acid are subsequently poured in over 10 minutes. The reaction mixture is stirred for an additional 15 minutes, and then 26 cm³ of water are poured in over 5 minutes, still at reflux. The suspension obtained is cooled to approximately 20° C. The precipitate is filtered off at approximately 20° C. and is washed with twice 10 cm³ of water. The moist product is dried under reduced pressure (20 kPa) at approximately 60° C. 1.25 g of crude 3-ethoxycarbonyl-7,8-difluoro-1-cyclopropyl-4-oxo-1,2,3,4-tetrahydro-1,8-benzo[b] naphthyridine are isolated, in the form of a yellow solid melting at 172° C.

Preparation of 3-ethoxycarbonyl-7,8-difluoro-1-cyclopropyl-4-oxo-1,4-dihydro-1,8-benzo[b]naphthyridine:

To a suspension of 1 g of 3-ethoxycarbonyl-7,8-difluoro-1-cyclopropyl-4-oxo-1,2,3,4-tetrahydro-1,8-benzo[b] naphthyridine in 14 cm³ of ethanol is added, with stirring at approximately 20° C., a solution of 0.053 g of potassium iodide in 0.5 cm³ of water. The suspension is heated to 77° C. and 0.5 cm³ of hydrogen peroxide at a concentration of 33% by weight is poured in over 5 minutes at this temperature. The reaction mixture is maintained at reflux for an additional 60 minutes and then cooled to approximately 20° C. At this temperature, 1.06 cm³ of 1N sodium thiosulphate solution are poured in over 5 minutes. The precipitate obtained is filtered off at approximately 20° C. and is washed with twice 10 cm³ of water. The moist product obtained is dried under reduced pressure (20 kPa) at approximately 60° C. 0.7 g of crude 3-ethoxycarbonyl-7,8-difluoro-1-cyclopropyl-4-oxo-1,4-dihydro-1,8-benzo[b]naphthyridine is obtained, in the form of a white ochre solid melting at 210° C.

Example of use 5

3-Ethoxycarbonyl-6,7-difluoro-2-(N-methyl-N-β-cyanoethylamino)quinoline is prepared in the following way:

To a solution of 16.3 g of 2-chloro-3-ethoxycarbonyl-6,7-difluoroquinoline prepared as described in Example 1 and 10 g of N-methyl-N-β-cyanoethylamine in 160 cm³ of toluene are added 19.08 g of sodium carbonate. The suspension obtained is heated at reflux and then stirred for 4 hours at this temperature. The reaction mixture is subsequently cooled to approximately 20° C., followed by washing with 3 times 50 cm³ of water. The organic phase is concentrated to dryness under reduced pressure (20 kPa) at approximately 50° C. 19.17 g of 3-ethoxycarbonyl-6,7-difluoro-2-(N-methyl-N-β-cyanoethylamino)quinoline are obtained in the form of an oil, which is used without further purification for the subsequent steps.

3-Cyano-7,8-difluoro-1-methyl-4-oxo-1,2,3,4-tetrahydro-1,8-benzo[b]naphthyridine is prepared in the following way:

To a solution of 8.74 g of potassium tert-butoxide in 200 cm³ of tetrahydrofuran, cooled to −10° C., is added over 60 minutes a solution of 19.17 g of 3-ethoxycarbonyl-6,7-difluoro-2-(N-methyl-N-β-cyanoethylamino)quinoline in 50 cm³ of tetrahydrofuran. The suspension obtained is stirred for an additional 30 minutes, still at −10° C. 4 cm³ of glacial acetic acid are subsequently poured in. The tetrahydrofuran is evaporated off under reduced pressure (20 kPa). The crude reaction mixture is taken up in 200 cm³ of an aqueous-alcoholic ethanol/water mixture (70/30 vol/vol). The precipitate obtained is filtered off, washed twice with 50 cm³ of water and then dried under reduced pressure (20 kPa). 16.1 g of 3-cyano-7,8-difluoro-1-methyl-4-oxo-1,2,3,4-tetrahydro-1,8-benzo[b]naphthyridine are isolated, in the form of a golden-yellow solid melting at 144° C.

3-Cyano-7,8-difluoro-1-methyl-4-oxo-1,4-dihydro-1,8-benzo[b]naphthyridine is prepared in the following way:

To a suspension of 8.6 g of 3-cyano-7,8-difluoro-1-methyl-4-oxo-1,2,3,4-tetrahydro-1,8-benzo[b] naphthyridine in 350 cm³ of ethanol is added, with stirring at approximately 20° C., a solution of 0.47 g of potassium iodide in 5 cm³ of water. The suspension is heated at 77° C., followed by addition thereto, at this temperature over 10 minutes, of 4 cm³ of hydrogen peroxide at a concentration of 33% by weight. The reaction mixture is maintained at reflux for an additional 30 minutes and then cooled to approximately 20° C. At this temperature, 10 cm³ of 1N sodium thiosulphate solution are added over 5 minutes. The precipitate obtained is filtered off at approximately 20° C. and is washed with twice 20 cm³ of water. The moist product obtained is dried under reduced pressure (20 kPa) at approximately 50° C. 8 g of 3-cyano-7,8-difluoro-1-methyl-4-oxo-1,4-dihydro-1,8-benzo[b]naphthyridine are isolated, in the form of a light yellow solid melting at 380° C.

3-Cyano-7-fluoro-1-methyl-8-(4-methyl-1-piperazinyl)-4-oxo-1,4-dihydro-1,8-benzo[b]naphthyridine is prepared in the following way:

A suspension of 2.1 g of 3-cyano-7,8-difluoro-1-methyl-4-oxo-1,4-dihydro-1,8-benzo[b]naphthyridine in 100 cm³ of dimethyl sulphoxide is heated at 80° C. in the presence of 2 cm³ of N-methylpiperazine. The reaction mixture is maintained at this temperature for 8 hours. The solution obtained is cooled to room temperature and stirred at this temperature for 15 hours. The precipitate formed is filtered off, washed with 3 times 20 cm³ of water and dried under vacuum (20 kPa) at 50° C. 2.6 g of 3-cyano-7-fluoro-1-methyl-8-(4-methyl-1-piperazinyl)-4-oxo-1,8-benzo[b]naphthyridine are obtained, in the form of a yellow precipitate melting at 335° C.

7-Fluoro-1-methyl-8-(4-methyl-1-piperazinyl)-4-oxo-1,4-dihydro-1,8-benzo[b]naphthyridine-3-carboxylic acid is prepared in the following way:

A suspension of 2 g of 3-cyano-7-fluoro-1-methyl-8-(4-methyl-1-piperazinyl)-4-oxo-1,4-dihydro-1,8-benzo[b]naphthyridine is heated at reflux in 40 cm³ of 12N hydrochloric acid. The reaction mixture is maintained at this temperature for 15 hours. The solution obtained is cooled to room temperature. The product which crystallizes is filtered off, washed with water until neutral, and dried under reduced pressure (20 kPa) at 50° C. 1.5 g of 7-fluoro-1-methyl-8-(4-methyl-1-piperazinyl)-4-oxo-1,4-dihydro-1,8-benzo[b] naphthyridine-3-carboxylic acid monohydrochloride are formed, in the form of yellow crystals melting at 290° C. (decomposition).

Example of use 6

3-Ethoxycarbonyl-6,7-difluoro-2-[N-methyl-N-β-(N',N'-dimethylaminocarbonylethyl)amino]quinoline is prepared in the following way:

To a solution of 26 g of 2-chloro-3-ethoxycarbonyl-6,7-difluoroquinoline prepared as described in Example 1 and 25 g of N-methyl-N-β-(N',N'-dimethylaminocarbonyl) ethylamine in 300 cm³ of toluene are added 31 g of sodium carbonate. The suspension obtained is heated to reflux and then stirred for 2 hours 30 minutes at this temperature. The reaction mixture is subsequently cooled to approximately 20° C., followed by washing with 3 times 100 cm³ of water. The organic phase is concentrated to dryness under reduced pressure (20 kPa) at approximately 50° C. 35 g of 3-ethoxycarbonyl-6,7-difluoro-2-[N-methyl-N-β-(N',N'-dimethylaminocarbonylethyl)amino]quinoline are obtained in the form of an oil, which is used without further purification for the subsequent steps.

N,N-Dimethyl-7,8-difluoro-1-methyl-4-oxo-1,2,3,4-tetrahydro-1,8-benzo[b]naphthyridine-3carboxamide is prepared in the following way:

To a solution of 15.7 g of potassium tert-butoxide in 150 cm³ of tetrahydrofuran, cooled to 0° C., is added, over 75 minutes, a solution of 35 g of 3-ethoxycarbonyl-6,7-difluoro-2-[N-methyl-N-β-(N',N'-dimethylaminocarbonylethyl)amino]quinoline in 150 cm³ of tetrahydrofuran. The suspension obtained is subsequently stirred at 0° C. for an additional 30 minutes, followed by addition of 8 cm³ of glacial acetic acid. The tetrahydrofuran is evaporated off under reduced pressure (20 kPa). The crude reaction mixture is taken up in 200 cm³ of an aqueous-alcoholic ethanol/water mixture (70/30 vol/vol). The precipitate obtained is filtered off, washed 3 times with 100 cm³ of water and then dried under vacuum (20 kPa). 25 g of N,N-dimethyl-7,8-difluoro-1-methyl-4-oxo-1,2,3,4-tetrahydro-1,8-benzo[b]naphthyridine-3-carboxamide are isolated, in the form of a lemon yellow solid melting at 206° C.

N,N-Dimethyl-7,8-difluoro-1-methyl-4-oxo-1,4-dihydro-1,8-benzo[b]naphthyridine-3-carboxamide is prepared in the following way:

To a suspension of 25 g of N,N-dimethyl-7,8-difluoro-1-methyl-4-oxo-1,2,3,4-tetrahydro-1,8-benzo[b] naphthyridine-3-carboxamide in 1000 cm³ of ethanol is added, with stirring at approximately 20° C., a solution of 1.35 g of potassium iodide in 10 cm³ of water. The suspension is heated to 77° C. and 25 cm³ of hydrogen peroxide at a concentration of 33% by weight are poured in at this temperature over 20 minutes. The reaction mixture is maintained at reflux for an additional 1 hour 30 minutes and then cooled to approximately 20° C. At this temperature, 30 cm³ of 1N sodium thiosulphate solution are run in over 5 minutes. The precipitate obtained is filtered off at approximately 20° C. and is washed with twice 60 cm³ of water. The moist product obtained is dried under reduced pressure (20 kPa) at approximately 50° C. 19.5 g of N,N-dimethyl-7,8-difluoro-1-methyl-4-oxo-1,4-dihydro-1,8-benzo[b] naphthyridine-3-carboxamide are isolated, in the form of a light yellow solid melting at 324° C.

A suspension of 2.96 g of 7,8-difluoro-N,N-dimethyl-4-oxo-1-methyl-1,4-dihydro-1,8-benzo[b]-naphthyridine-3-carboxamide, 1.12 g of 1-methylpiperazine and 1.55 g of potassium carbonate in 100 cm³ of dimethyl sulphoxide is heated for 5 hours at approximately 80° C., with stirring. After cooling to approximately 20° C., 100 cm³ of water are added to the reaction mixture; the insoluble product is filtered off, and washed with twice 30 cm³ of water and twice 30 cm³ of ethanol.

2.3 g of N,N-dimethyl-7-fluoro-1-methyl-8-(4-methyl-1-piperazinyl)-4-oxo-1,4-dihydro-1,8-benzo[b]-naphthyridine-3-carboxamide are obtained, in the form of a yellow solid decomposing at 275° C.

A solution of 0.5 g of N,N-dimethyl-7-fluoro-1-methyl-8-(4-methyl-1-piperazinyl)-4-oxo-1,4-dihydro-1,8-benzo[b] naphthyridine-3-carboxamide in 10 cm³ of 6N aqueous hydrochloric acid is heated to approximately 95° C., with stirring, for 5 hours. After cooling to approximately 20° C., the insoluble product is filtered off, and washed with 3 times 20 cm³ of water and twice 10 cm³ of ethanol.

The product obtained is suspended in 30 cm³ of water; 0.6 cm³ of 1N aqueous potassium hydroxide is added and stirring is carried out for 1 hour at approximately 20° C. The insoluble product is filtered off, and washed with twice 20 cm³ of water and twice 10 cm³ of ethanol. After recrystallization in 15 cm³ of dimethylformamide, 0.15 g of 7-fluoro-1-methyl-8-(4-methyl-1-piperazinyl)-4-oxo-1,4-dihydro-1,8-benzo[b]naphthyridine-3-carboxylic acid is obtained, in the form of a yellow solid decomposing at 354° C.

Example of use 7

3-Ethoxycarbonyl-6,7-difluoro-2-(N-methyl-N-β-aminocarbonylethylamino)quinoline is prepared in the following way:

To a solution of 4 g of 2-chloro-3-ethoxycarbonyl-6,7-difluoroquinoline prepared as described in Example 1 and 3 g of N-methyl-N-β-aminocarbonylethylamine in 40 cm³ of toluene are added 4.4 g of sodium carbonate. The suspension obtained is heated to reflux and then stirred for 2 hours 30 minutes at this temperature. The reaction mixture is subsequently cooled to approximately 20° C., followed by washing with 3 times 25 cm³ of water. The organic phase is concentrated to dryness under reduced pressure (20 kPa) at approximately 50° C. 4.7 g of 3-ethoxycarbonyl-6,7-difluoro-2-(N-methyl-N-β-aminocarbonylethylamino) quinoline are obtained in the form of an oil, which is used without further purification for the subsequent steps.

7,8-Difluoro-1-methyl-4-oxo-1,2,3,4-tetrahydro-1,8-benzo[b]naphthyridine-3-carboxamide is prepared in the following way:

To a solution of 1.8 g of potassium tert-butoxide in 50 cm³ of tetrahydrofuran cooled to 0° C. is added, over 30 minutes, a solution of 4.23 g of 3-ethoxycarbonyl-6,7-difluoro-2-(N-methyl-N-β-aminocarbonylethylamino) quinoline in 20 cm³ of tetrahydrofuran. The suspension obtained is subsequently stirred at 0° C. for an additional 30 minutes and then 2 cm³ of glacial acetic acid are poured in. The tetrahydrofuran is evaporated off under reduced pressure (20 kPa). The crude reaction mixture is taken up in 10 cm³ of an aqueous-alcoholic ethanol/water mixture (70/30 vol/vol). The precipitate obtained is filtered off, washed with 3 times 10 cm³ of water, and then dried under reduced pressure (20 kPa). 1.6 g of 7,8-difluoro-1-methyl-4-oxo-1,2,3,4-tetrahydro-1,8-benzo[b]napthyridine-3-carboxamide are isolated, in the form of a yellow solid melting at 182° C.

3-Carboxamido-7,8-difluoro-1-methyl-4-oxo-1,4-dihydro-1,8-benzo[b]naphthyridine is prepared in the following way:

To a suspension of 1.3 g of 3-carboxamido-7,8-difluoro-1-methyl-4-oxo-1,2,3,4-tetrahydro-1,8-benzo[b]napthyridine in 25 cm³ of ethanol is added, with stirring at approximately 20° C., a solution of 0.1 g of potassium iodide in 1 cm³ of water. The suspension is heated to 77° C. and 1.5 cm³ of hydrogen peroxide at a concentration of 33% by weight is added thereto over 5 minutes at this temperature. The reaction mixture is maintained at reflux for an additional 1 hour 30 minutes, followed by cooling to approximately 20° C. At this temperature, 1 cm³ of 1N sodium thiosulphate solution is added. The precipitate obtained is filtered off at approximately 20° C. and is washed with twice 5 cm³ of water. The moist product obtained is dried under reduced pressure (20 kPa) at approximately 50° C. 1.1 g of 3-carboxamido-7,8-difluoro-1-methyl-4-oxo-1,4-dihydro-1,8-benzo[b]naphthyridine are isolated, in the form of an orange-coloured solid melting at 318° C.

A suspension of 1.3 g of 7,8-difluoro-1-methyl-4-oxo-1,4-dihydro-18-benzo[b]naphthyridine-3-carboxamide, 0.54 g of 1-methylpiperazine and 0.75 g of potassium carbonate in 25 cm³ of dimethyl sulphoxide is heated at approximately 80° C. for 6 hours. After cooling to a temperature in the region of 20° C., 100 cm³ of water are added to the reaction mixture. The insoluble product is filtered off, and washed with twice 20 cm³ of water and twice 20 cm³ of ethanol.

The product obtained is chromatographed on 20 g of silica gel (0.063–0.200 mm) suspended in a mixture of dichloromethane containing 10% of methanol. The reaction impurities are removed by eluting with 500 cm³ of this mixture of solvents. The expected product is subsequently eluted with 500 cm³ of the same mixture of solvents. After concentrating to dryness under reduced pressure (20 kPa) at approximately 40° C., the solid residue is crystallized in 25 cm³ of dimethylformamide, filtered off and washed with twice 30 cm³ of ethanol at approximately 70° C.

0.6 g of 7-fluoro-1-methyl-8-(4-methyl-1-piperazine)-4-oxo-1,4-dihydro-1,8-benzo[b]naphthyridine-3-carboxamide is obtained, in the form of a yellow solid decomposing at 265° C.

7-Fluoro-8-(4-methyl-1-piperazinyl)-1-methyl-4-oxo-1,4-dihydro-1,8-benzo[b]naphthyridine-3-carboxylic acid is prepared under the conditions of Example of use 2, but starting from 0.3 g of 7-fluoro-1-methyl-8-(4-methyl-1-piperazinyl)-4-oxo-1,4-dihydro-1,8-benzo[b]naphthyridine-3-carboxamide. After cooling to approximately 20° C., 50 cm³ of water are added to the reaction mixture; the insoluble product is filtered off and washed with twice 10 cm³ of water.

The product obtained is suspended in 20 cm³ of water, 0.4 cm³ of 1N aqueous potassium hydroxide solution is added thereto and stirring is carried out for 1 hour at approximately 20° C. The insoluble product is filtered off, washed with 3 times 10 cm³ of water and twice 10 cm³ of ethanol and recrystallized in 20 cm³ of dimethylformamide.

0.17 g of 7-fluoro-1-methyl-8-(4-methyl-1-piperazinyl)-4-oxo-1,4-dihydro-1,8-benzo[b]naphthyridine-3-carboxylic acid is obtained, in the form of a yellow solid decomposing at 354° C.

We claim:

1. A process for the preparation of a 6-fluoro-2-haloquinoline of general formula (I)

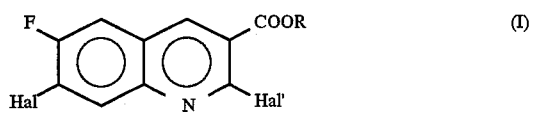

in which R is a hydrogen atom or an alkyl radical, and Hal and Hal' are identical or different halogen atoms, said process characterized in that a halogenating agent is reacted with the 1-hydroxyquinolone of general formula:

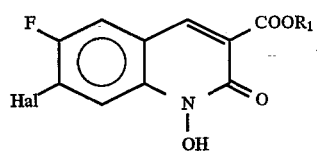

in which Hal is defined as above and $R_1$ is defined as R with the exception of representing a hydrogen atom, optionally followed by freeing the acidic function if it is desired to obtain a 6-fluoro-2-haloquinoline for which R is a hydrogen atom.

2. A process for the preparation of a 6-fluoro-2-haloquinoline according to claim 1, characterized in that the symbol Hal is chlorine or fluorine and the symbol Hal' is chlorine or bromine.

3. A process for the preparation of a 6-fluoro-2-haloquinoline according to either of claims 1 and 2, characterized in that the halogenating agent is chosen from phosphorus trichloride, phosphorus pentachloride, thionyl chloride, sulphuryl chloride, sulphur dichloride, stannous chloride, cuprous chloride, titanium trichloride, ferrous chloride, chromium(II) chloride, triphenylphosphine hydrochloride, dichlorotriphenylphosphorane, chlorine, phosphorus tribromide, triphenylphosphine hydrobromide or dibromotriphenylphosphorane.

4. A process for the preparation of a 6-fluoro-2-haloquinoline according to claim 1, said process further comprising preparing the starting 1-hydroxyquinolone by cyclizing a
nitro derivative of formula (III):

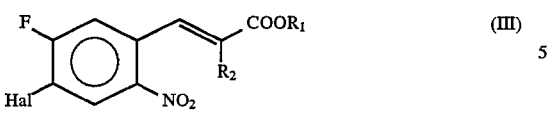

in which Hal and $R_1$ are defined as in claim 1, and $R_2$ is defined as $R_1$ or represents a carbamoyl or cyano radical, by catalytic hydrogenation in acidic medium.

5. A method for the preparation of a 1,8-benzo[b] naphthyridine derivative of formula (VII):

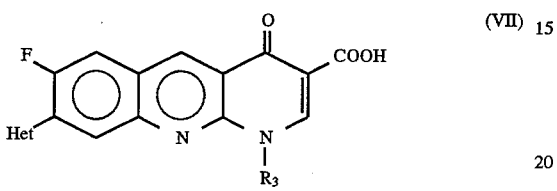

in which when $R_3$ is an alkyl, fluoroalkyl, cycloalkyl containing 3 to 6 carbon atoms, alkyloxy or alkylamino radical and then Het is a nitrogen-containing heterocyclic radical, or when $R_3$ is a hydrogen atom or an alkyl, fluoroalkyl, carboxyalkyl, cycloalkyl containing 3 to 6 carbon atoms, fluorophenyl, difluorophenyl, alkyloxy or alkylamino radical, then Het is a 1-azetidinyl radical which is substituted in the 3-position with a radical $R_4$ which may be a hydrogen atom or a hydroxyl, amino, or alkylamino radical in which the alkyl part is optionally substituted with an amino or hydroxyl radical or $R_4$ represents a dialkylamino radical for which the alkyl parts optionally form, with the nitrogen atom to which they are attached, a 5- or 6-membered heterocycle optionally containing another hetero atom selected from nitrogen, oxygen, and sulphur, or $R_4$ represents a cycloalkylamino radical containing 3 to 6 members, or an alkanoylamino, N-alkyl-N-alkanoylamino or aminoalkylphenylamino radical, and substituted in the 2- and 3-positions with radicals $R_5$ and $R_6$, which are identical or different and which represent hydrogen atoms, alkyl radicals, alkenyl radicals containing 2 to 4 carbon atoms, phenyl radicals or phenyl radicals substituted with a halogen atom, or with an alkyl, alkyloxy, hydroxyl, nitro, amino, alkylamino, dialkylamino or haloalkyl radical, or alternatively disubstituted in the 2-position with radicals $R_5$ and $R_6$ which represent alkyl radicals, the alkyl and alkanoyl radicals mentioned above being straight or branched and containing 1 to 4 carbon atoms comprising the steps of:

cyclizing a nitro derivative of formula (III)

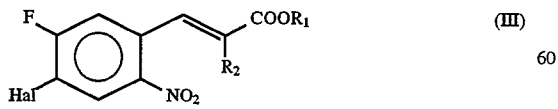

in which Hal is a halogen atom, $R_1$ is an alkyl radical, and $R_2$ is an alkyl radical, a carbamoyl radical, or a cyano radical, by catalytic hydrogenation in acidic medium to form a 1-hydroxyquinoline of the formula (II)

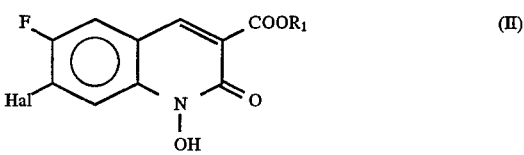

in which Hal is a halogen atom and $R_1$ is an alkyl radical, converting said 1-hydroxyquinoline under conditions sufficient to form a 6-fluoro-2-haloquinoline of the formula (I)

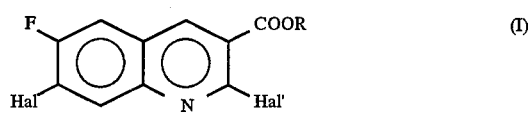

in which R is a hydrogen atom, and Hal and Hal' are identical or different halogen atoms; and converting said 6-fluoro-2-haloquinoline under conditions sufficient to form said 1,8-benzo[b] naphthyridine derivative of formula (VII).

6. A method for the preparation of a benzonaphthyridine derivative of formula (XI):

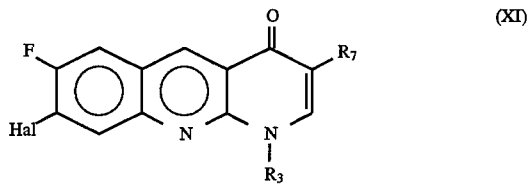

in which Hal is a halogen atom, $R_3$ represents a hydrogen atom or an alkyl, fluoroalkyl, carboxyalkyl, cycloalkyl containing 3 to 6 carbon atoms, fluorophenyl, difluorophenyl, alkyloxy or alkylamino radical and $R_7$ is an alkyloxycarbonyl, cyano, carbamoyl, alkylcarbamoyl, benzylcarbamoyl, hydroxyethylcarbamoyl, dialkylaminoethylcarbamoyl or dialkylcarbamoyl radical in which the alkyl parts may optionally form, with the nitrogen atom to which they are attached, a 5-or 6-membered heterocycle optionally containing another hetero atom selected from oxygen, sulphur, and nitrogen and optionally substituted on the nitrogen with an alkyl radical, the alkyl radical being straight or branched and containing 1 to 4 carbon atoms comprising the steps of:

cyclizing a nitro derivative of formula (III)

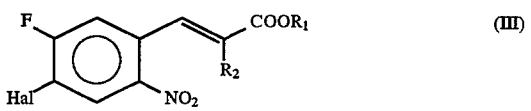

in which Hal is as defined above, $R_1$ is an alkyl radical, and $R_2$ is an alkyl radical, a carbamoyl radical, or a cyano radical, by catalytic hydrogenation in acidic medium to form a 1-hydroxyquinoline of the formula (II):.

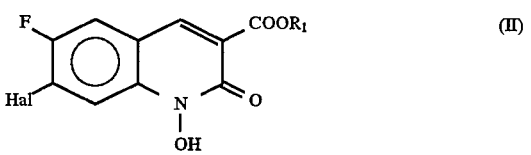

in which Hal is a halogen atom and $R_1$ is an alkyl radical, converting said 1-hydroxyquinoline under conditions sufficient to form a 6-fluoro-2-haloquinoline of the formula (I)

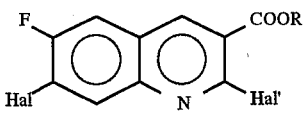

in which R is a hydrogen atom, Hal and Hal' are identical or different halogen atoms; and converting said 6-fluoro-2-haloquinoline of the formula (I) with an amine of the formula (VIII)

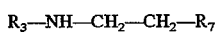

in which $R_3$ and $R_7$ are defined as above under conditions sufficient to obtain a fluoroester of formula (IX):

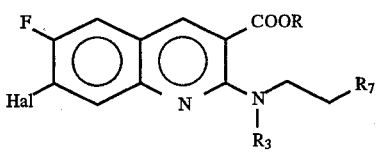

in which Hal, $R_3$, and $R_7$ are as defined above and R is an alkyl group;

cyclizing said fluoroester of formula (IX) under conditions sufficient to prepare a 1,2,3,4,-tetrahydro-1,8-benzo[b]naphthyridine of formula (X)

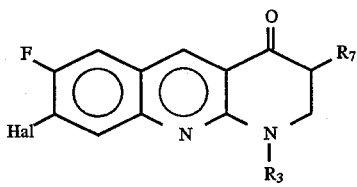

in which Hal, $R_3$ and $R_7$ are as defined above; and converting said 1,2,3,4,-tetrahydro-1,8-benzonaphthyridine of formula (X) under conditions sufficient to form said benzo[b]naphthyridine derivative of formula (XI).

7. A method for the preparation of a 1,8-benzonaphthyridine derivative of formula (VII):

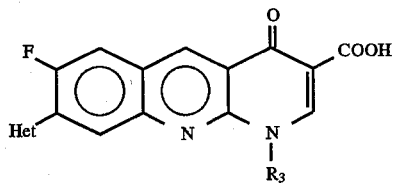

in which when $R_3$ is an alkyl, fluoroalkyl, cycloalkyl containing 3 to 6 carbon atoms, alkyloxy or alkylamino radical, then Het is a nitrogen-containing heterocyclic radical, or when $R_3$ is a hydrogen atom or an alkyl, fluoroalkyl, carboxyalkyl, cycloalkyl containing 3 to 6 carbon atoms, fluorophenyl, difluorophenyl, alkyloxy or alkylamino radical, then Het is a 1-azetidinyl radical which is substituted in the 3-position with a radical $R_4$ which may be a hydrogen atom or a hydroxyl, amino, or alkylamino radical in which the alkyl part is optionally substituted with an amino or hydroxyl radical or $R_4$ represents a dialkylamino radical for which the alkyl parts optionally form, with the nitrogen atom to which they are attached, a 5- or 6-membered heterocycle optionally containing another hetero atom selected from nitrogen, oxygen, and sulphur, or $R_4$ represents a cycloalkylamino radical containing 3 to 6 members, or an alkanoylamino, N-alkyl-N-alkanoylamino or aminoalkylphenylamino radical, and substituted in the 2- and 3- positions with radicals $R_5$ and $R_6$, which are identical or different and which represent hydrogen atoms, alkyl radicals, alkenyl radicals containing 2 to 4 carbon atoms, phenyl radicals or phenyl radicals substituted with a halogen atom, or with an alkyl, alkyloxy, hydroxyl, nitro, amino, alkylamino, dialkylamino or haloalkyl radical, or alternatively disubstituted in the 2-position with radicals $R_5$ and $R_6$ which represent alkyl radicals, the alkyl and alkanoyl radicals mentioned above being straight or branched and containing 1 to 4 carbon atoms comprising the steps of:

cyclizing a nitro derivative of formula (III)

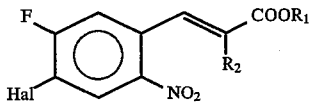

in which Hal is a halogen atom, $R_1$ is an alkyl radical, and $R_2$ is an alkyl radical, a carbamoyl radical, or a cyano radical, by catalytic hydrogenation in acidic medium to form a 1-hydroxyquinoline of the formula (II)

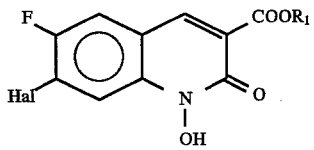

in which Hal is a halogen atom and $R_1$ is an alkyl radical, and converting said 1-hydroxyquinoline under conditions sufficient to form said 1,8-benzonaphthyridine derivative of formula (VII).

8. A method for the preparation of a benzonaphthyridine derivative of formula (XI):

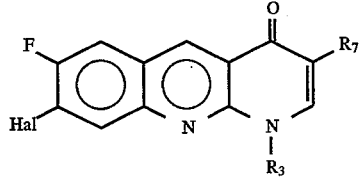

in which Hal is a halogen atom, $R_3$ represents a hydrogen atom or an alkyl, fluoroalkyl, carboxyalkyl, cycloalkyl containing 3 to 6 carbon atoms, fluorophenyl, difluorophenyl, alkyloxy or alkylamino radical and $R_7$ is an alkyloxycarbonyl, cyano, carbamoyl, alkylcarbamoyl, benzylcarbamoyl, hydroxyethylcarbamoyl, dialkylaminoethylcarbamoyl or dialkylcarbamoyl radical in which the alkyl parts may optionally form, with the nitrogen atom to which they are attached, a 5- or 6-membered heterocycle optionally containing another hetero atom selected from oxygen, sulphur, and nitrogen and optionally substituted on the nitrogen with an alkyl radical, the alkyl radical being straight or branched and containing 1 to 4 carbon atoms comprising the steps of:

cyclizing a nitro derivative of formula (III)

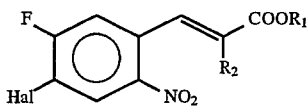

in which Hal is as defined above, $R_1$ is an alkyl radical, and $R_2$ is an alkyl radical, a carbamoyl radical, or a cyano radical, by catalytic hydrogenation in acidic medium to form a 1-hydroxyquinoline of the formula (II):

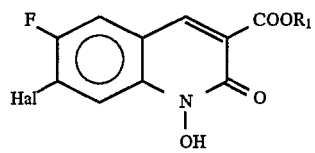

in which Hal is a halogen atom and $R_1$ is an alkyl radical, converting said 1-hydroxyquinoline under conditions sufficient to form said benzonaphthyridine derivative of formula (XI).

* * * * *

UNITED STATES PATENT AND TRADEMARK OFFICE
CERTIFICATE OF CORRECTION

Page 1 of 2

PATENT NO. : 5,624,933
DATED : April 29, 1997
INVENTOR(S) : Hervé GARCIA et al.

It is certified that error appears in the above-indentified patent and that said Letters Patent is hereby corrected as shown below:

Title page, item [54], and col. 1, line 2 of the title, FLUORO-2-HALO-QUINOLINE" should read --FLUORO-2-HALOGEN QUINOLINE--.

Title page, item [75], after "Inventors", "Herve Garcia" should read --Hervé Garcia--.

Title page, item [22], "PCT Filed: Oct. 20, 1994" should read --PCT Filed: April 7, 1994--.

Title page, item [86], "PCT No.: PCT/US94/11832" should read --PCT No.: PCT/FR94/00391--.

Claim 5, column 15, line 12, "1,8-benzo]b]" should read --1,8-benzo[b]--.

UNITED STATES PATENT AND TRADEMARK OFFICE
CERTIFICATE OF CORRECTION

PATENT NO. : 5,624,933
DATED : April 29, 1997
INVENTOR(S) : Hervé GARCIA et al.

It is certified that error appears in the above-indentified patent and that said Letters Patent is hereby corrected as shown below:

Claim 6, column 16, line 58, "(II):." should read
--(II):--;
      column 17, line 42, "benzonaphthyridine" should read --benzo[b]naphthyridine--; and
      line 43, "benzo[b]naphthyridine" should read --benzonaphthyridine--.

Claim 7, column 17, line 46, "benzonaphthyridine" should read--benzo[b]naphthyridine--; and
      column 18, line 46, "1,8-benzonaphthyridine" should read --1,8-benzo[b]naphthyridine--.

Signed and Sealed this

Twenty-fourth Day of March, 1998

*Attest:*

BRUCE LEHMAN

*Attesting Officer*     *Commissioner of Patents and Trademarks*